United States Patent
Striemer et al.

(10) Patent No.: US 10,668,436 B2
(45) Date of Patent: Jun. 2, 2020

(54) METHODS FOR CREATING FLUIDIC CAVITIES BY TRANSMEMBRANE ETCHING THROUGH POROUS MEMBRANES AND STRUCTURES MADE THEREBY AND USES OF SUCH STRUCTURES

(71) Applicant: SiMPore Inc., West Henrietta, NY (US)

(72) Inventors: Christopher C. Striemer, Rochester, NY (US); Joshua J. Miller, Rochester, NY (US); Jon-Paul S. Desormeaux, Rochester, NY (US); James A. Roussie, Rochester, NY (US)

(73) Assignee: SiMPore Inc., West Henrietta, NY (US)

( * ) Notice: Subject to any disclaimer, the term of this patent is extended or adjusted under 35 U.S.C. 154(b) by 0 days.

(21) Appl. No.: 15/772,488

(22) PCT Filed: Oct. 31, 2016

(86) PCT No.: PCT/US2016/059741
§ 371 (c)(1),
(2) Date: Apr. 30, 2018

(87) PCT Pub. No.: WO2017/075598
PCT Pub. Date: May 4, 2017

(65) Prior Publication Data
US 2018/0304206 A1   Oct. 25, 2018

Related U.S. Application Data

(60) Provisional application No. 62/248,467, filed on Oct. 30, 2015.

(51) Int. Cl.
*B01D 67/00*     (2006.01)
*B01D 69/02*     (2006.01)
(Continued)

(52) U.S. Cl.
CPC ....... *B01D 67/0062* (2013.01); *B01D 61/243* (2013.01); *B01D 69/02* (2013.01);
(Continued)

(58) Field of Classification Search
CPC ....... C23F 1/00; B01D 67/0062; B01D 61/14; B01D 61/24; B01D 61/243;
(Continued)

(56) References Cited

U.S. PATENT DOCUMENTS 7,128,843 B2   10/2006   Mehta
7,784,619 B2    8/2010   Jacobson
(Continued)

FOREIGN PATENT DOCUMENTS

WO    2015023966 A1   2/2015

*Primary Examiner* — Alexander S Thomas
(74) *Attorney, Agent, or Firm* — Hodgson Russ LLP

(57) ABSTRACT

Provided are monolithic structures comprising one or more suspended, nanoporous membranes that are in contact with one or more fluidic cavities, methods of making same, and exemplary uses of same. The monolithic structures can be formed using a transmembrane etch. The monolithic structures can be used, as examples, as filters and filtration modules in microfluidic devices, dialysis devices, and concentration devices in laboratory, industrial, and medical processes.

5 Claims, 10 Drawing Sheets

(51) Int. Cl.
*B01D 61/24* (2006.01)
*B01D 69/12* (2006.01)
*B01D 71/02* (2006.01)
*B81C 1/00* (2006.01)
*C12M 1/12* (2006.01)
*C12M 1/26* (2006.01)
*G01N 1/34* (2006.01)
*G03F 7/00* (2006.01)
*B01D 61/18* (2006.01)
*C23F 1/04* (2006.01)

(52) U.S. Cl.
CPC ............ *B01D 69/12* (2013.01); *B01D 71/02* (2013.01); *B01D 71/021* (2013.01); *B01D 71/027* (2013.01); *B81C 1/00119* (2013.01); *C12M 25/02* (2013.01); *C12M 33/14* (2013.01); *G01N 1/34* (2013.01); *G03F 7/0015* (2013.01); *B01D 61/18* (2013.01); *B01D 2325/028* (2013.01); *B81B 2201/014* (2013.01); *B81B 2201/058* (2013.01); *B81B 2203/0315* (2013.01); *B81B 2203/0338* (2013.01); *B81B 2203/0353* (2013.01); *B81C 2201/0115* (2013.01); *C23F 1/04* (2013.01)

(58) Field of Classification Search
CPC ......... B01D 2325/028; B81C 1/00119; C12M 25/02; C12M 33/14
USPC ...................................................... 216/2, 41
See application file for complete search history.

(56) References Cited

U.S. PATENT DOCUMENTS

| | | |
|---|---|---|
| 8,518,276 B2 | 8/2013 | Striemer et al. |
| 8,834,730 B2 | 9/2014 | Lee et al. |
| 2004/0124092 A1 | 7/2004 | Black et al. |
| 2015/0139401 A1 | 5/2015 | Ribbing et al. |

METHODS FOR CREATING FLUIDIC CAVITIES BY TRANSMEMBRANE ETCHING THROUGH POROUS MEMBRANES AND STRUCTURES MADE THEREBY AND USES OF SUCH STRUCTURES

CROSS REFERENCE TO RELATED APPLICATIONS

This application claims priority to U.S. Provisional Application No. 62/248,467 filed on Oct. 30, 2015, the disclosure of which is hereby incorporated by reference.

FIELD OF THE DISCLOSURE

The disclosure generally relates to methods of creating fluidic cavities. More particularly, the disclosure relates to methods of creating fluidic cavities using transmembrane etching through porous membranes.

BACKGROUND OF THE DISCLOSURE

A through-wafer etch step is presently required to expose and suspend active-area porous nanomembranes. Porous nanomembranes are typically less than 100 nm thick and, thus, are restricted to less than 1 mm in one dimension in most embodiments to maintain their integrity and resistance to mechanical forces such as differential pressure or handling during assembly into exemplary devices. This restriction limits the amount of active membrane area available for functional applications.

The use of wet chemical etching with, for example, ethylenediamine pyrocatechol (EDP), to expose and suspend porous nanomembranes disposed on a Si wafer, results in approximately 55° sloping side-walls of openings etched through <1-0-0> orientation Si wafers due to its anisotropic etching. This characteristic constrains the number of active membranes that can be placed side-by-side within a device, and thus, physically limits the active membrane area that can be incorporated with <1-0-0> wafers. Alternative Si orientations such as <1-1-0> would permit through-wafer etching with straight side-walls, thus closer spacing between suspended membranes. However, the distance between the suspended membrane and the through-wafer opening (i.e., the Si wafer thickness), as well as the overall device geometry, would both remain less than optimal.

Etching through the entire thickness of the Si wafer is also required to define both outer chip dimensions and suspended membrane active area. The thickness of the Si wafer remnant imposes significant and unnecessary additional volume between the suspended, porous nanomembrane and the through-wafer opening. This problem is further exaggerated when gasketing material is bonded to the through-wafer-etched side of a device for fluidic purposes, since the gaskets inevitably contribute additional thickness, volume, and step-heights. This increases diffusional distances and, consequently, reduces mass transfer rates when porous nanomembranes are used in filtration or separation applications. Thus, device geometry and etching method improvements are needed to improve mass transfer capacity within devices incorporating porous nanomembranes.

SUMMARY OF THE DISCLOSURE

In an aspect, the present disclosure provides methods of making the monolithic structures. The methods are based on fabrication of one or more layers comprising one or more suspended membranes (e.g., suspended, porous membranes, such as suspended nanoporous membranes or suspended, microporous membranes) on a substrate via a transmembrane etch and, optionally, etching the side of the substrate opposite of the one or more layers of suspended membranes. In an embodiment, a monolithic structure of the present disclosure is made by a method disclosed herein. Monolithic structures with multiple layers comprising one or more suspended, nanoporous membranes may be formed. These structures can be formed by repeating the process steps used to form a layer comprising one or more suspended, nanoporous membranes.

The dimensions, size and placement of the through-wafer-etched features can be specified as desired. For example, two through-wafer-etched features could be patterned and etched perpendicularly to, and at the distal ends of, the transmembrane-etched trenches. One or more additional through-wafer-etched features could be similarly patterned along the length of, and perpendicularly to, the transmembrane-etched trenches. In these embodiments, multiple trenches are fluidically accessed and connected to the through-wafer-etched features. In other embodiments, through-wafer-etched features could be patterned and etched parallel to transmembrane-etched trenches. In this embodiment, one or more transmembrane-etched trenches could be fluidically accessed and connected to a through-wafer-etched feature. In these embodiments, the extent of both transmembrane-etching and through-wafer etching could be specified to control the amount of substrate etched by either processes. For instance, one-third of the upper portion of the substrate could be etched by transmembrane etching, while two-thirds could be etched by through-wafer etching. Any possible combination could be specified as desired.

In an aspect, the present disclosure provides monolithic structures. The monolithic structures comprise one or more suspended, nanoporous membranes and/or microporous membranes that may be in contact with one or more channels (trenches). The monolithic structures are not formed from two or more structures/devices. The monolithic structure may be a fluidic structure. In an embodiment, a monolithic structure is made by a method of the present disclosure or combination of steps of methods of the present disclosure.

These monolithic fluidic structures may be useful, among other applications, as: 1) dialysis modules for clinical and laboratory research and medical devices; 2) cell growth bioreactors; 3) filtration modules for laboratory and industrial processes; and 4) pre-filtration/concentration modules for sample preparation upstream of sensors/detectors.

In an aspect, the present disclosure provides a device comprising a monolithic structure of the present disclosure or a monolithic structure made using a method of the present disclosure. The device may have one or a plurality of such structures.

For example, the device is a filtration device. In an embodiment, the device is a filtration module for a laboratory or industrial process. In another embodiment, the device is a pre-concentration/concentration module for a laboratory or industrial process. In yet another embodiment, the device is a blood dialysis or extracorporeal membrane blood oxygenation module. In another embodiment, the devices having two suspended, porous membranes can serve as a fractionator of mixtures of differently sized solutes within a solution. In an embodiment, the device is a cell growth bioreactor. In an embodiment, the device can be used as a pre-filter upstream of detector and sensor devices.

BRIEF DESCRIPTION OF THE FIGURES

For a fuller understanding of the nature and objects of the disclosure, reference should be made to the following detailed description taken in conjunction with the accompanying figures.

FIG. 9 is a close up view of the undercut after 10 pulses. FIG. 10 is a full trench width side profile after 10 pulses of $XeF_2$. FIG. 11 is a side profile of the corresponding etch parameters. FIG. 12 is a top-down image of 4 pulses. FIG. 13 is a close up view of the under-cut and the nanoporous detail.

DETAILED DESCRIPTION OF THE DISCLOSURE

Figure 1:
FIGS. 1-8 are cross-sectional views of structures formed during an embodiment of the instant method of forming a monolithic structure with fluidic cavities.
Figure 2:
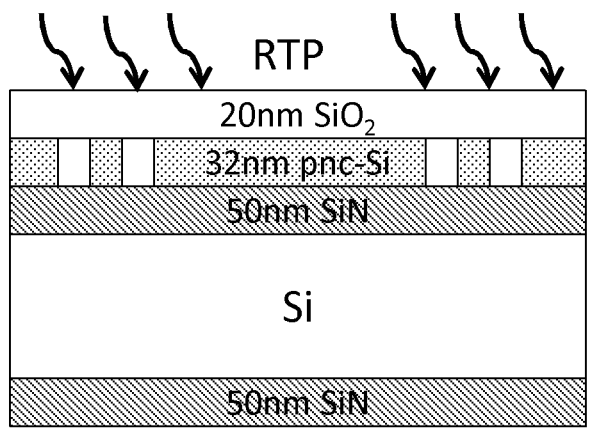
Figure 3:
Figure 4:
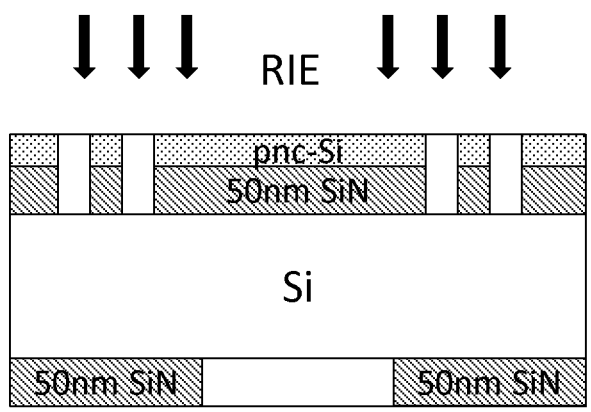
Figure 5:
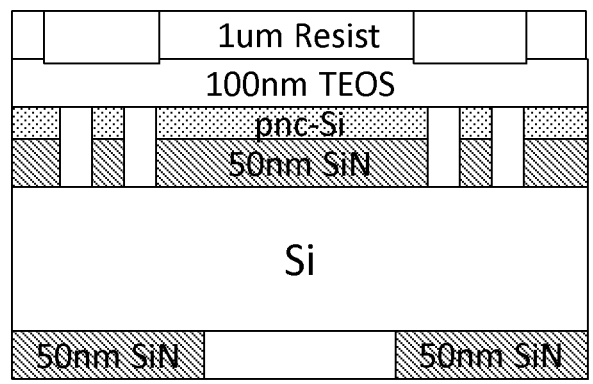
Figure 6:
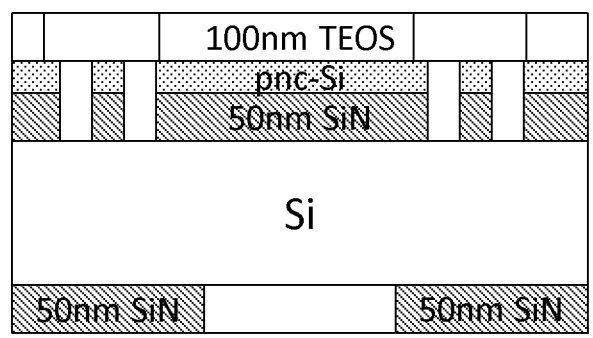
Figure 7:
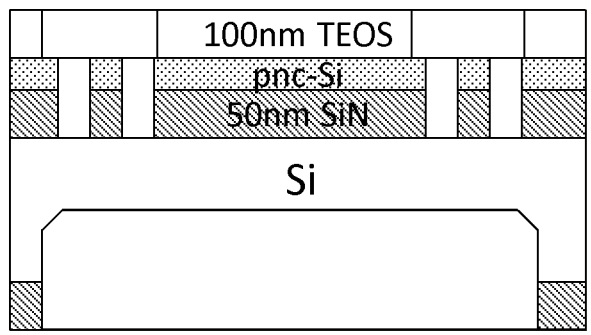

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides structures comprising one or more suspended membranes (e.g., suspended, non-porous membranes and/or suspended, porous (e.g., nanoporous and/or microporous) membranes) that are in contact with one or more trenches (that can be fluidic channels). The disclosure also provides methods of making the structures and methods of using the structures. The structures can be referred to as monolithic structures.

This disclosure describes methods for the fabrication of monolithic structures comprising suspended membranes enclosing (i.e., in fluid contact with) voids that can be used as fluidic channels. For example, the structures comprise one or more suspended, porous (e.g., nanoporous and/or microporous) membranes disposed on a substrate, e.g., a Si wafer substrate, or a second suspended membrane, which may be either non-porous or porous (e.g., nanoporous or microporous) within the substrate. In various examples, the structure comprises a layer comprising one or more suspended, porous (e.g., nanoporous and/or microporous) membranes (e.g., silicon nitride membranes), disposed on a substrate and/or one or more layers, each layer comprising one or more suspended, porous (e.g., nanoporous and/or microporous) membranes (e.g., silicon nitride membranes), disposed on a layer disposed on a substrate (assuming the substrate is considered the bottom (e.g., side opposite the layer) of the structure).

In the case where there are multiple suspended membranes, the individual membranes may be in fluid contact with one or more other membranes in the structure. The individual membranes may be in fluid contact with one or more other membranes in the same layer (i.e., intralayer fluid contact) or different layers (i.e., interlayer fluid contact) of the structure. In the case where there are multiple layers of suspended membranes, the individual layers may be in fluid contact through a void in a discrete via and/or spacer layer.

These monolithic fluidic structures may be useful, among other applications, as: 1) dialysis modules for clinical and laboratory research and medical devices; 2) cell growth bioreactors; 3) filtration modules for laboratory and industrial processes; and 4) pre-filtration/concentration modules for sample preparation upstream of sensors/detectors.

The present disclosure provides methods for removal of sacrificial material (e.g., substrate material and/or spacer material) by a transmembrane etch, through an in situ fabricated porous membrane (e.g., a nanoporous or microporous membrane) to create trench or fluidic cavity structures (and as a result the porous membrane becomes a suspended, porous membrane). The suspended, porous membrane (e.g., suspended, nanoporous or microporous membrane) can also be referred to as a free-standing, porous membrane. The present disclosure also provides structures made using this transmembrane etching method.

Porous nanomembranes through which the transmembrane etching can be performed are known in the art. For example, a porous nanomembrane through which the transmembrane etching is performed can be nanoporous silicon nitride (NPN), created as described in U.S. patent application Ser. No. 14/911,879, which is hereby incorporated by reference in its entirety. Accordingly, in an example, the structures comprise one or more suspended, nanoporous silicon nitride (NPN) membranes above (if the substrate is considered the bottom of the structure) a substrate, e.g., a Si wafer substrate, or a second suspended, membrane, which may be either non-porous or porous, within the substrate.

In an aspect, the present disclosure provides methods of making the monolithic structures. The methods are based on fabrication of one or more layers comprising one or more suspended membranes (e.g., suspended, porous membranes, such as suspended nanoporous membranes or suspended, microporous membranes) on a substrate via a transmembrane etch and, optionally, etching the side of the substrate opposite of the one or more layers of suspended membranes. In an embodiment, a monolithic structure of the present disclosure is made by a method disclosed herein.

In an embodiment, a NPN membrane is created on a first surface of a substrate (e.g., a Si wafer substrate). In another embodiment, a NPN film is created on a layer disposed on the substrate (e.g., a spacer layer) and a third distal membrane layer is deposited on the first surface of the substrate. The spacer layer proximally underlying the NPN membrane serves as a sacrificial material layer, while any third distal layer serves as a possible second suspended membrane, to be created during through-wafer etch described herein.

In an embodiment, the method for forming a monolithic structure comprising one or more suspended, nanoporous membranes comprises:

a) depositing a first membrane material layer (e.g., silicon nitride) on a first side of a substrate (e.g., a crystalline silicon wafer);

b) depositing a layer of masking material (e.g., silicon nitride) on a second side of the substrate;

c) depositing a first pre-patterning layer (amorphous silicon) on the first membrane material layer;

d) depositing a first layer of capping material (e.g., silicon oxide) on the first pre-patterning layer;

e) forming a first patterning layer (from the first pre-patterning layer) by thermal treatment of substrate that includes the first pre-patterning layer (forming pnc-Si from the amorphous silicon layer via thermal treatment);

f) removing the first capping material;

g) patterning the first membrane material layer (to form a nanoporous membrane material) by pattern transfer from the first patterning layer (e.g., by reactive ion etch);

h) optionally, removing the first patterning layer (in certain instances it may be desirable to remove the first patterning layer);

i) depositing a first layer of via material (e.g., silicon oxide) on the patterned first membrane material layer;

j) patterning the first layer of via material (e.g., deposit photoresist, pattern photoresist, selectively etch silicon oxide, and remove photoresist) such that at least a portion of the patterned first membrane material layer is exposed; and k) patterning the masking material from b), such that at least a portion of the substrate is exposed, removing at least a portion of the substrate by etching with silicon etchants (e.g., EDP, KOH, TMAH, or $XeF_2$) through the patterned first membrane material and the masking material, such that the substrate material corresponding to at least the portion of patterned first membrane material that was exposed is removed and an underlying trench and first suspended, nanoporous membrane are formed, and such that the substrate material corresponding to at least the portion of patterned masking material that was exposed is removed and a fluidic cavity is formed that is fluidically connected to the trench. In an embodiment, both of the options in k) for etching through the substrate to form fluidic cavities, underlying trenches, and first suspended, nanoporous membranes are carried out. In an embodiment, i) (optionally) and j) and k) are repeated to provide different patterns of suspended, nanoporous membranes and underlying trenches. In an embodiment, the steps of forming the first suspended, nanoporous membrane and/or one or more additional suspended, nanoporous membranes are modified such that a first suspended, microporous membrane and/or one or more additional suspended, microporous membranes are formed. In various embodiments, the method comprises formation of one or more layers comprising one or more suspended, non-porous membranes, by omitting steps c) through l) with respect to processing of the first membrane layer(s). In various embodiments, the first membrane layer comprises patterned regions of both nanoporous and microporous membranes within the same layer.

In another embodiment, the method of the previous embodiment further comprises depositing a photoresist on the first patterning layer of the first surface of the substrate from f), patterning the photoresist, selectively transferring the pattern of the first patterning layer into the first membrane layer as in g), removing the photoresist, and performing the transmembrane- and through-wafer etch as in k), such that the substrate material corresponding to at least a portion of patterned first membrane material layer (as defined by the patterned photoresist on the first patterning layer during pattern transfer) is removed to form an underlying trench and a first suspended, nanoporous membrane, and such that the substrate material corresponding to at least a portion of patterned masking material layer is removed to form through-wafer-etched features.

Monolithic structures with multiple layers comprising one or more suspended, nanoporous membranes may be formed. These structures can be formed by repeating the process steps used to form a layer comprising one or more suspended, nanoporous membranes. Accordingly, in an embodiment, the method of the previous two embodiments, further comprises:

l) depositing a spacer layer of sacrificial material (e.g., silicon, silicon oxide, or other readily removed or dissolved material) on the substrate from k) (forming a continuous layer over the first patterned via layer);

m) depositing a second membrane material layer (e.g., silicon nitride) on the spacer layer of sacrificial material;

n) depositing a second pre-patterning layer (amorphous silicon) on the second membrane material layer;

o) depositing a second layer of capping material (e.g., silicon oxide) on the second pre-patterning layer;

p) forming a second patterning layer (from the second pre-patterning layer) by thermal treatment of substrate that includes the second pre-patterning layer (forming pnc-Si from the amorphous silicon layer using thermal treatment);

q) removing all or substantially all of the second layer of capping material (e.g., silicon oxide);

r) patterning the second membrane material by pattern transfer from the second patterning layer by reactive ion etch) to form a nanoporous membrane;

s) optionally, removing all or substantially all of the second patterning layer;

t) depositing a second layer of via material (e.g. silicon oxide);

u) patterning the second layer of via material (e.g., deposit photoresist, pattern photoresist, selectively etch silicon oxide, and remove photoresist) such that at least a portion of the patterned second layer of membrane material is exposed;

v) removing the sacrificial material such that a second suspended, nanoporous membrane is formed (etching through the patterned second membrane layer to remove at least a portion of the sacrificial material and forming a trench or a continuous fluidic cavity from the patterned area of the via material), wherein the second suspended, nanoporous membrane may be in fluid contact with the first suspended, nanoporous membrane; and w) optionally, repeating l) to v) to form one or more additional suspended, nanoporous membranes, wherein one or more of the suspended, nanoporous membranes may be in fluid contact with one or more of other suspended, nanoporous membranes. In an embodiment, the steps of forming the second suspended, nanoporous membrane and/or one or more additional suspended, nanoporous membranes are modified such that a second suspended, microporous membrane and/or one or more additional suspended, microporous membranes are formed. In various embodiments, the method comprises formation of one or more layers comprising one or more suspended, non-porous membranes.

One having skill in the art will appreciate that the steps of the methods described herein may be performed in the sequence described and, in certain cases, in a different sequence than described. In an embodiment, the steps in the above embodiment are carried out sequentially. In various embodiments, these process steps can be carried out in different sequences. For example, etching the substrate through the exposed masking material can be performed prior to etching the substrate through the exposed first membrane layer. As another example, etching the substrate through the exposed first membrane layer can be performed prior to etching the substrate through the exposed masking layer.

The membrane layers (e.g., first nanoporous membrane layer and second nanoporous membrane layer) (e.g., NPN layers) comprise materials that are patternable (e.g., using photolithographic processes known in the art), form uniform (e.g., nanoscale uniform or microscale uniform) films, that are electron transparent, can be deposited on the substrate, and are inert to processes (e.g., to process chemicals used in the processes) used in the methods. The membrane layer may be continuous or have discrete regions. The membrane layers can be formed from a variety of materials. Examples of suitable materials include silicon nitride, silicon oxide, any other combination of silicon and other elements, or any other material that is resistant to typical silicon etchants. The membranes may be non-porous, nanoporous, or microporous. The embedded distal membrane may be non-porous. Microporous membranes are formed with well-known lithographic processes that are familiar to those skilled in the art. A single nanopore may be formed by methods that are familiar to those skilled in the art, such as focused-ion beam drilling, e-beam lithography and reactive ion etching or capacitive dielectric breakdown, the latter described in U.S. patent application Ser. No. 14/399,071, which is hereby incorporated by reference in its entirety. The suspended membrane layer can have a range of thickness. For example, the thickness of the membrane can be from 10 nm to 100 nm, including all values to the nm and ranges therebetween. Of course, other thickness values are possible and these are merely listed as examples. The individual suspended, porous membrane layers can have a range of pore size and porosity. For example, the membrane could have no pores or one or more pores ranging in diameter from 10 nm to 50 µm, including all nm diameters values and ranges therebetween. The membrane could range in porosity from 0% through 75%, with all possible porosities in between. Of course, other thickness values and/or porosity are possible and these are merely listed as examples. The suspended membrane layer(s) are formed from the membrane layers as is known in the art and described herein.

Examples of materials in which trenches are formed that are removed during the transmembrane etch could include substrate materials (e.g., mono-crystalline Si of a Si wafer substrate), poly-crystalline Si, silicon dioxide, among others. If deposited as the spacer layer as described herein, the thickness of this layer will determine the space between, for example, the NPN and third distal membranes.

Various etchants for removing substrate and/or sacrificial material to form trenches and fluidic cavities can be used. Suitable etchants for the particular substrate or sacrificial material are known in the art. For example, etchants for etching mono- and poly-crystalline Si include potassium hydroxide (KOH), ethylenediamine pyrocatechol (EDP), tetramethyl-ammonium hydroxide (TMAH), xenon difluoride ($XeF_2$), and other well-known silicon etchants. Etchants for etching silicon dioxide include hydrofluoric acid (HF) and buffered-oxide etchant (BOE), and other silicon dioxide etchants. The etchants access the materials to be removed through the pores of the uppermost film of the structure, and initially etch down into and laterally through the substrate and sacrificial material. In various embodiments, single and/or multiple trenches are created within the structures using only a portion of or the entirety of a substrate (e.g., a Si wafer substrate).

Methods that are familiar to those skilled in the art can be used to promote the uniformity of the transmembrane etch, such as the inclusion of oxygen ($O_2$) gas or surfactants (e.g., ionic and non-ionic detergents or low surface tension solvents) at a range of concentrations within the substrate and sacrificial material etchant solutions. Similarly, the uniformity of the transmembrane etch may be improved by initial transmembrane etch using $XeF_2$ followed by completion of the transmembrane etch using wet etchants appropriate for the substrate or sacrificial material.

The trench can have various shapes and dimensions. Based on the etch parameters (e.g., type of etch, duration, temperature, etc.) a trench or trenches of a selected shape and dimension can be formed. For example, the longest dimension of the trench can be from, 1 µm to Si wafer diameter (e.g., 200 mm, 300 mm, 450 mm), including all integer µm values therebetween, or 1 mm to Si wafer diameter, including all integer mm values therebetween.

In an embodiment, a membrane layer (e.g., a NPN membrane) is overlaid with a suitable patterning layer and patterned using well-known photolithography and etching methods (e.g., j) in the embodiment above). Examples of this overlaid patterning layer may include, for example, silicon oxide, a photoresist, or a fluoropolymer, among others. The number and dimensions of openings in this layer determine the number and dimensions of resulting transmembrane-etched trenches. Patterned openings in this patterning layer expose regions where the transmembrane etch will occur; i.e., exposed regions of NPN membrane corresponding to at least a portion of the substrate or sacrificial material where transmembrane etching will remove such underlying material. If desired, the patterning layer can be removed by any method appropriate for its composition after completion of the transmembrane etch. In various embodiments, the overlaid patterning layer may serve as a via layer in fluidic contact with the trenches and suspended, nanoporous membranes, wherein the suspended, nanoporous membranes have a plurality of pores that are fluidically connected with the trenches. Upon completion of the transmembrane etch, for example, the NPN membrane layer becomes a suspended membrane and the upper portion of the monolithic structure.

If no third distal membrane layer is included and the transmembrane etch was performed into the Si wafer substrate, then the bottom portion of the trench (assuming the substrate is the bottom of the structure) is defined by the Si wafer substrate at this step in the process.

The dimensions of the patterned openings to expose the membrane layer, e.g., NPN membrane layer, as well as the thickness and composition of the sacrificial material, the etchant, and the duration of the transmembrane etch, will determine the size and shape of the trench underlying the membrane layer, e.g., NPN membrane layer. Thus, these parameters can be manipulated to specify the characteristics of the trenches as desired. For example, the trenches may be 100 µm wide and 100 µm deep, having sloped side-walls, when transmembrane etching is performed using KOH, EDP, or TMAH, into the Si wafer substrate. Alternatively, the trenches may be 10 µm wide and 100 µm deep, with roughly straight side-walls, when performing the through-pore etch using $XeF_2$ into a 100 nm thick sacrificial layer of polycrystalline silicon. Of course, many iterations of these trench size and shape characteristics can be achieved.

To gain fluidic access to the trenches, well-known photolithography patterning and through-wafer etching is used. The patterning and through-wafer etching is accomplished on a second surface of the Si wafer substrate opposite to the surface on which transmembrane etch was accomplished. Once etched, these through-wafer features connect to the laterally etched, trenches created by the transmembrane etch. The through-wafer etch may be accomplished prior to, or after, the transmembrane etch step. An additional deposition or passivation layer may be required between the through-wafer and transmembrane etches to prevent over-etching through the transmembrane-etched channel during the through-wafer etch process. For example, if the through-wafer etch is performed first, then a thermally grown silicon oxide layer can be created on the through-wafer etched features to prevent over-etching during transmembrane etch. Of course, other passivation methods can be employed using materials resistant to silicon etchants.

Any additional distal membrane layer that may comprise the lower portion of the structure, if incorporated, can also become a second suspended membrane layer, comprising the lower portion of the trench.

The dimensions, size and placement of the through-wafer-etched features can be specified as desired. For example, two through-wafer-etched features could be patterned and etched perpendicularly to, and at the distal ends of, the transmembrane-etched trenches. One or more additional through-wafer-etched features could be similarly patterned along the length of, and perpendicularly to, the transmembrane-etched trenches. In these embodiments, multiple trenches are fluidically accessed and connected to the through-wafer-etched features.

In other embodiments, through-wafer-etched features could be patterned and etched parallel to transmembrane-etched trenches. In this embodiment, one or more transmembrane-etched trenches could be fluidically accessed and connected to a through-wafer-etched feature. In these embodiments, the extent of both transmembrane-etching and through-wafer etching could be specified to control the amount of substrate etched by either processes. For instance, one-third of the upper portion of the substrate could be etched by transmembrane etching, while two-thirds could be etched by through-wafer etching. Any possible combination could be specified as desired.

A variety of substrates can be used. An example of a suitable substrate material is silicon. Substrates typically used in conventional semiconductor fabrication processes can be used. For example, silicon substrates can be used. In an embodiment, a 100 mm, 150 mm, 200 mm, 250 mm, 300 mm, or 450 mm silicon wafer can be used. The monolithic structure can cover a portion of the substrate or substantially all of the substrate. Other substrates may be used including Ge, $SiO_2$, GaAs, silicon-on-insulator (SOI), etc.

The masking layer provides a mask for the etching of the substrate (e.g., k) in the embodiment above). This layer is disposed on the second surface of the substrate, is patterned and selectively removed, and the portions of the layer that are removed define the position and size of the through-wafer-etched features (i.e., fluidic cavities connecting to transmembrane-etched trenches). The masking layer can be formed from a variety of materials. Examples of suitable masking layer materials include silicon nitride, silicon oxide, a photoresist, and a fluoropolymer. The thickness of the masking layer can be from nanometers to several microns thick. For example, the masking layer has a thickness of 20 nm to 2 microns, including all integer nm values and ranges therebetween.

The pre-patterning layer provides a material that can be used to form the patterning material that has nanoporous structure that can be transferred to the membrane material layer. For example, the patterning layer is formed by first depositing amorphous silicon (the pre-patterning layer) that forms porous, nanocrystalline silicon (pnc-Si; the patterning layer) on thermal treatment. Suitable thermal treatments for the first pre-patterning layer that form the patterning layer include, for example, Rapid Thermal Anneal (RTA), furnace treatment, flash lamp anneal, laser anneal and the like. The nanoporous membranes are formed by pattern transfer from the pre-patterning layer. Dimensions are coupled to substrate size as described herein.

The capping materials are deposited on the pre-patterning layer. This layer provides the etch-stop and physical constraint during thermal treatment. It is desirable that this material be resistant to the silicon etchants and differ from the underlying porous membrane.

The spacer layer of sacrificial material provides structures that are in fluid contact with two or more of the suspended, nanoporous membranes. Examples of suitable sacrificial materials include silicon (e.g., crystalline or polycrystalline silicon) and silicon oxide. The thickness of this layer may be related to the desired channel thickness.

The various layers in the methods can be deposited by methods known in the art. Examples of suitable deposition methods include (low-pressure chemical vapor deposition (LPCVD), plasma-enhanced chemical vapor deposition (PECVD), evaporation, atomic layer deposition (ALD), sputtering, spin coating, dip coating, and spray coating. Different methods can be used to deposit different layers in a method.

Patterning steps in the method can be carried out by methods known in the art. Examples of suitable patterning methods include lithographic methods (e.g., photolithographic methods) followed by reactive ion etch (RIE) or chemical etch, or liftoff processes. The photolithographic patterning methods can be positive-tone methods or negative-tone methods.

Etching steps in the method can be carried out by methods known in the art. The etching steps can be wet (e.g., EDP, KOH, or TMAH) etching) or dry (reactive ion etching). Examples of suitable etching methods include Buffered Oxide etch to remove oxides, RIE to remove SiN, and EDP/KOH or Deep reactive ion etch (DRIE) to etch through the silicon wafer.

The materials used in the methods, and in the structures/devices made by the methods, can be suitable for holding liquid samples, in particular, biological samples, and/or materials suitable for nanofabrication. Examples of suitable materials include dielectric materials such as silicon, silicon nitride and other nitrides, silicon dioxide and other oxides, graphene, carbon nanotubes, $TiO_2$, $HfO_2$, $Al_2O_3$, or other metallic layers, or any combination of these materials.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

In an aspect, the present disclosure provides monolithic structures. The monolithic structures comprise one or more suspended, nanoporous membranes and/or microporous membranes that may be in contact with one or more channels (trenches). The monolithic structures are not formed from two or more structures/devices. The monolithic structure may be a fluidic structure.

A monolithic structure comprising one or more suspended, porous membranes (e.g., suspended, nanoporous membranes, suspended, microporous membranes, or a combination of both types of membranes) is disclosed. The monolithic structure has, for example, a substrate, a patterned, first-membrane-material layer, a first layer of via material, and a layer of masking material. The substrate may be a crystalline silicon wafer and has a first side and opposing second side. The substrate may have a plurality of trenches. The patterned, first-membrane-material layer can be silicon nitride. The patterned, first-membrane-material layer is disposed on the first side of the substrate and has a plurality of pores fluidically connected to the trenches in the substrate. The first layer of via material is disposed on the patterned first membrane material. The first layer of via material can be silicon oxide and is patterned to have vias fluidically connected to the pores. The layer of masking material can be silicon nitride and is disposed on the second side of the substrate. The layer of masking material has at least one fluidic cavity that is fluidically connected with the trenches in the substrate.

The monolithic structure of the previous embodiment, wherein the via layer material is absent.

The monolithic structure may include a first patterning layer disposed between the patterned first membrane material layer and the first layer of via material. The first patterning layer may be pnc-Si and is patterned to fluidically connect the vias and the pores.

The masking material may have a plurality of fluidic cavities. Each of the trenches may be fluidically connected to different, or the same, fluidic cavity or cavities.

In an embodiment, a monolithic structure comprising a suspended, nanoporous membrane comprises: a substrate (e.g., a crystalline silicon wafer) having a first side and opposing second side, wherein the substrate has a plurality of trenches; a patterned first membrane material layer (e.g., silicon nitride) disposed on the first side of the substrate, wherein the patterned first membrane material layer has a plurality of pores fluidically connected to the trenches in the substrate; a first layer of via material (e.g., silicon oxide) disposed on the patterned first membrane material layer, wherein the first layer of via material is patterned to have vias fluidically connected to the pores; and a layer of masking material (e.g., silicon nitride) disposed on the second side of the substrate, wherein the layer of masking material has at least one fluidic cavity that is fluidically connected with the trenches in the substrate.

The monolithic structure of the previous embodiment, may further comprise: a first patterning layer (e.g., pnc-Si) disposed between the patterned first membrane material layer and the first layer of via material, wherein the first patterning layer is patterned to fluidically connect the vias and the pores. Optionally, the masking material has a plurality of the fluidic cavities, and wherein each of the trenches is fluidically connected to different fluidic cavities.

The monolithic structure of the previous embodiment may further comprise a spacer layer of sacrificial material (e.g., silicon or silicon oxide), a patterned second membrane material layer (e.g., silicon nitride), and a second layer of via material (e.g., silicon oxide). The spacer layer of sacrificial material has a first side and opposing second side and a plurality of trenches. The patterned second membrane material layer is disposed on the first side of the spacer layer and has a plurality of pores fluidically connected to the trenches in the spacer layer. The second layer of via material is disposed on the patterned second membrane material layer and is patterned to have vias fluidically connected to the pores of the patterned second membrane material layer. Optionally, the spacer layer may be disposed on the patterned first membrane material layer disposed on the first side of the substrate. Optionally, any second via layer can be absent. Optionally, the spacer layer may be disposed on the first layer of via material disposed on the patterned first membrane material layer. Additional spacer layer(s), patterned membrane material layer(s), and layer(s) of via materials also may be included.

Figure 8:
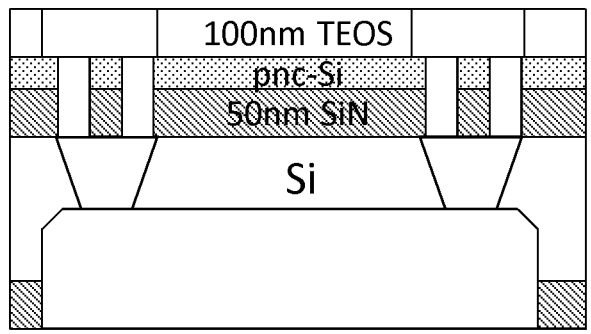
Figure 9:
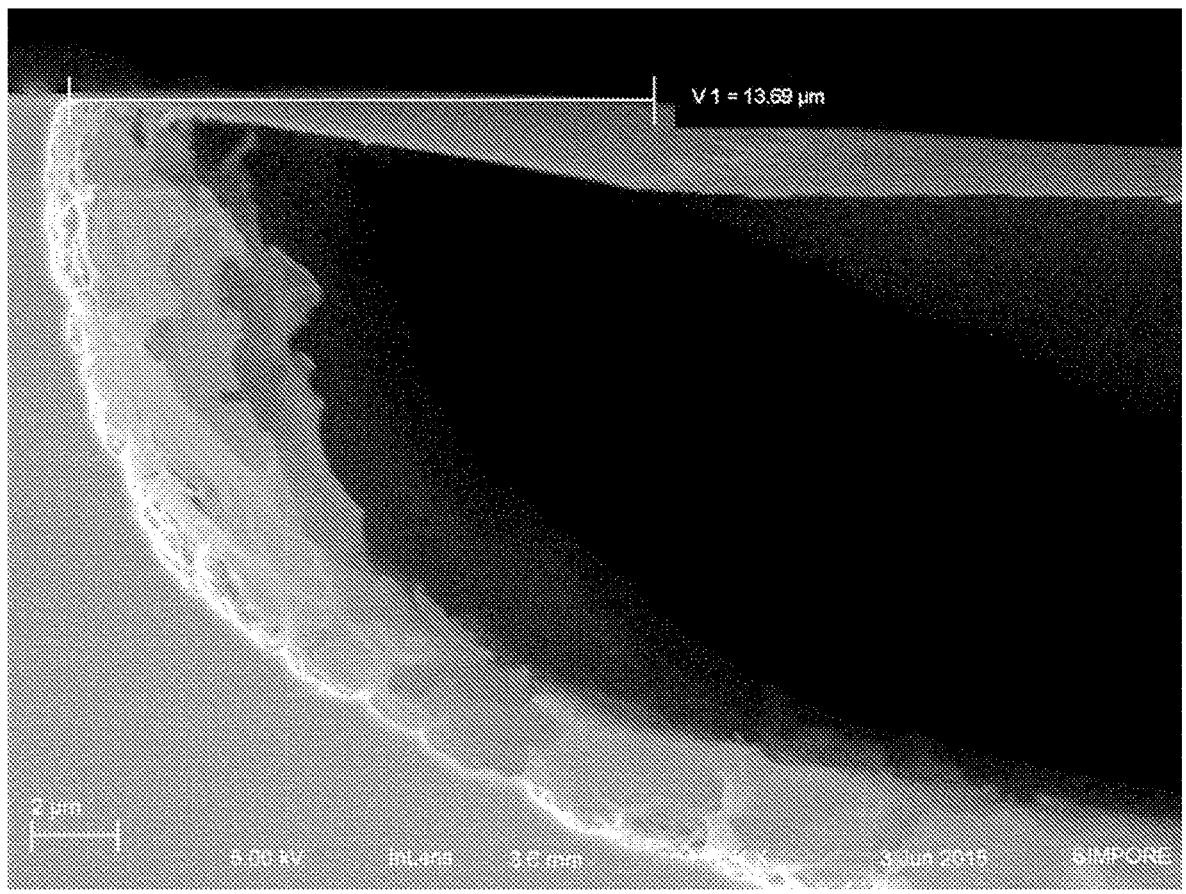
FIGS. 9-13 are representative scanning electron microscopy images of example structures formed by first etching through the Si wafer (from the side opposite the nanoporous silicon nitride) for approximately 3 hours in EDP. This created the through-wafer fluidic access to the trenches underlying the nanoporous silicon nitride. Next, the trenches were etched using $XeF_2$ for a variety of pulses. For all cases, pulses were 60 second duration and 3 Torr $XeF_2$.
Figure 10:
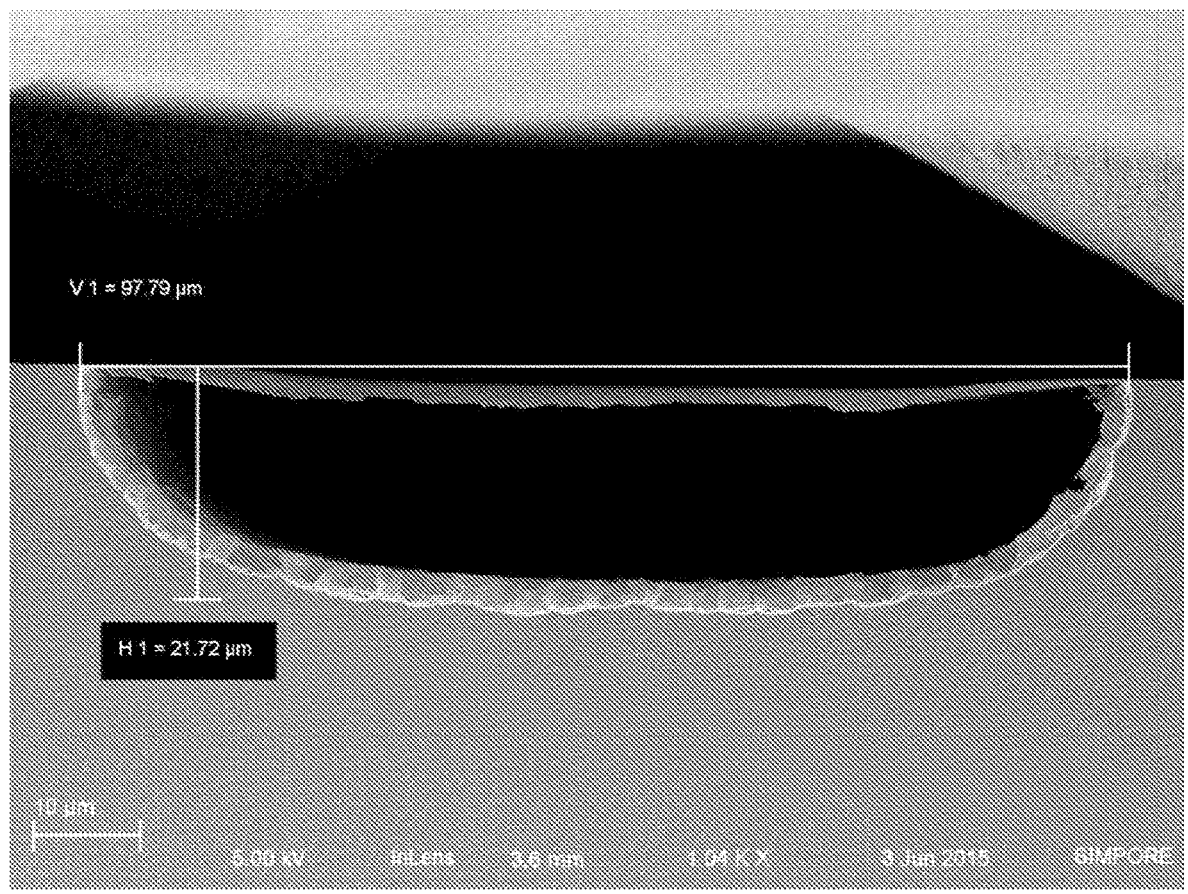
Figure 11:
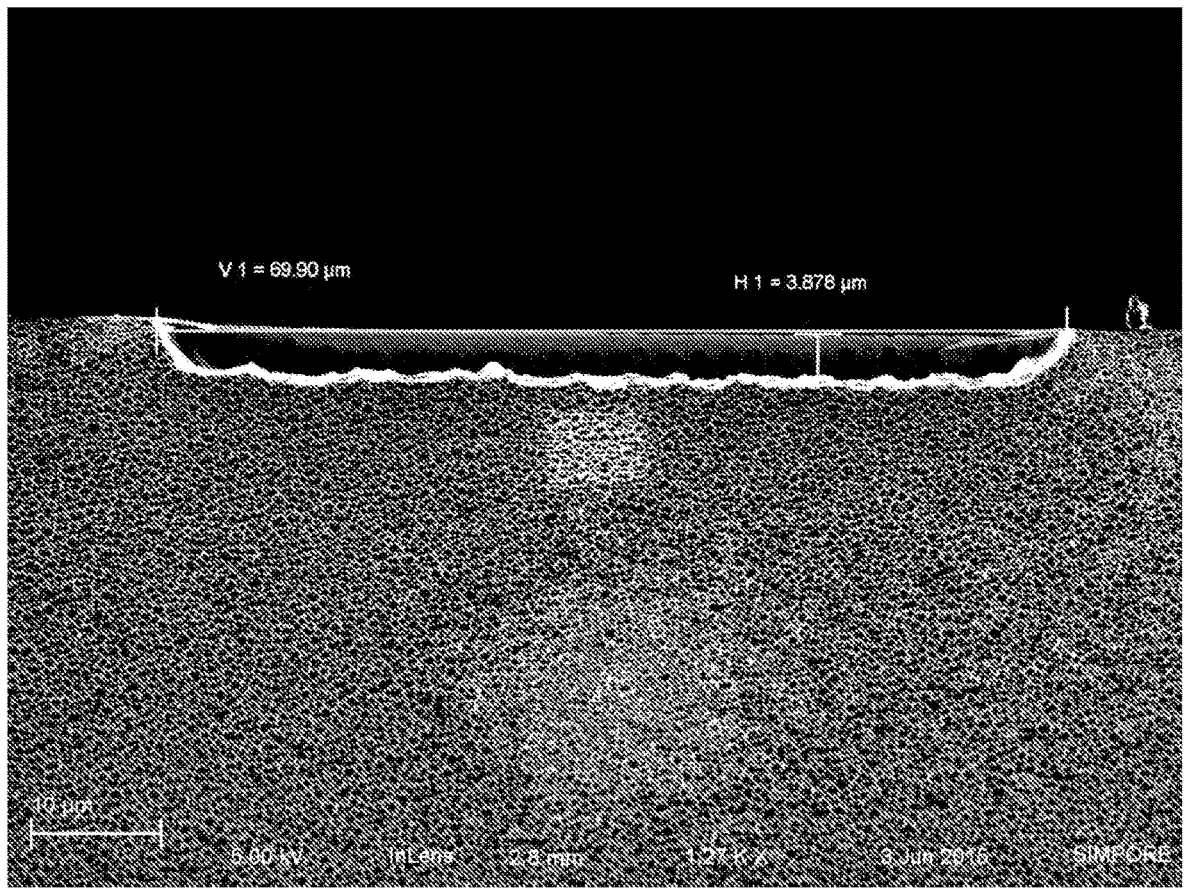
Figure 12:
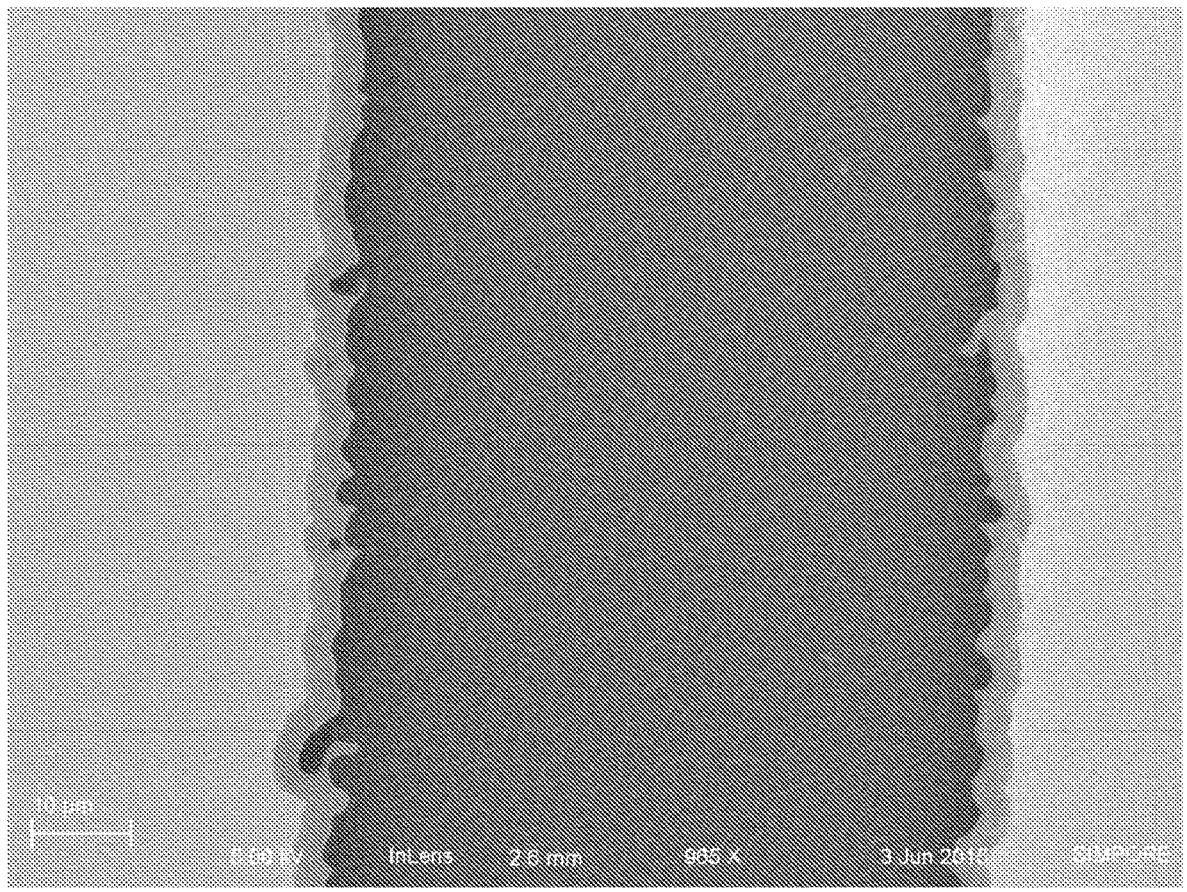
Figure 13:
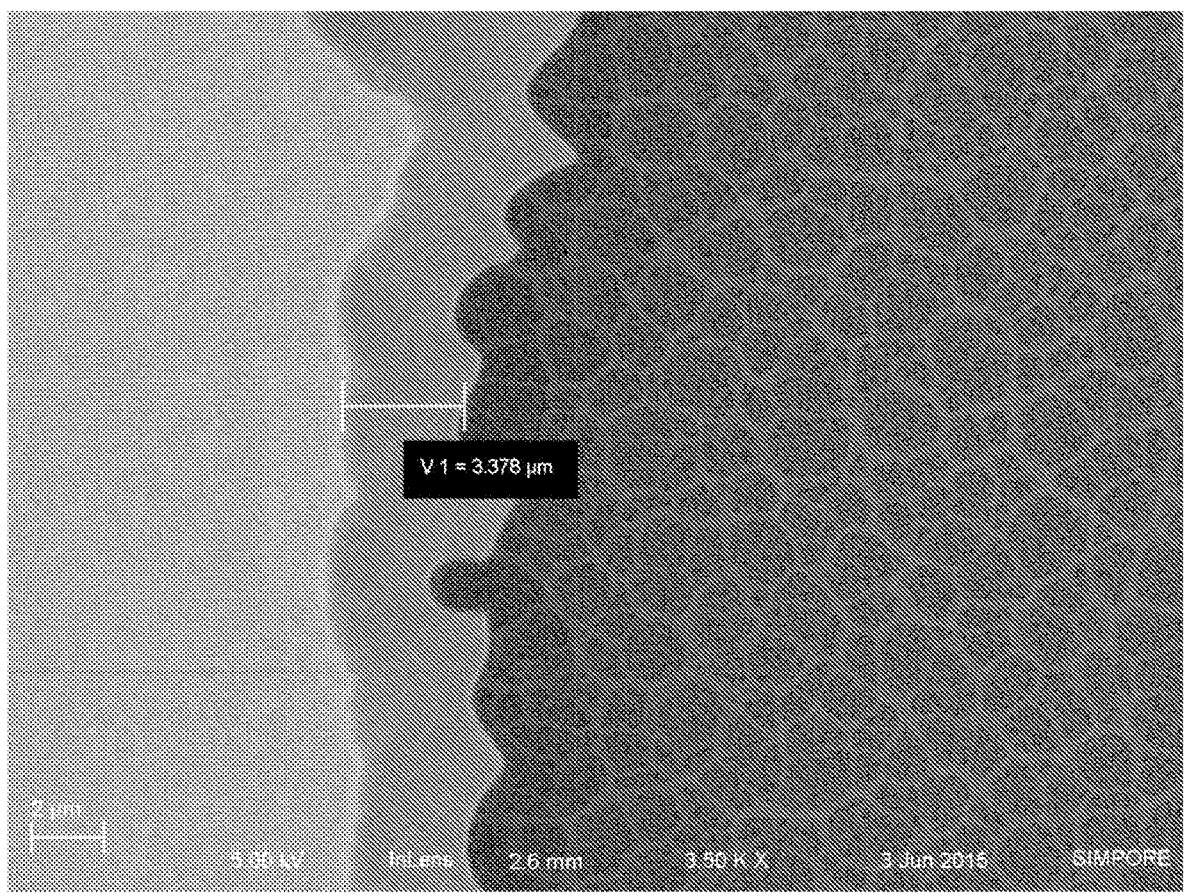

This first SiN layer can range in porosity. While the multiple trenches in FIG. 8 are illustrated as formed by isotropic etching, the trenches can be formed by anisotropic etching or may have smooth sides.

The number of cavities in the Si wafer can vary. For example, the Si wafer can have multiple cavities, each connected to one or more trenches connected to the pores in the SiN layer. In an example, each cavity is connected to a different set of trenches. Different parts of the Si wafer can be masked to form different cavities.

The dimensions, size, and placement of the through-wafer-etched features can be specified as desired. For example, two through-wafer-etched features could be patterned and etched perpendicularly to, and at the distal ends of, the transmembrane-etched trenches. One or more additional through-wafer-etched features could be similarly patterned along the length of, and perpendicularly to, the transmembrane-etched trenches. In these embodiments, multiple trenches are fluidically accessed and connected to the through-wafer-etched features. While the fluidic structure in FIG. 8 is shown in cross-section, the cavities and trenches can be formed in three dimensions. Thus, the cavity (or cavities) of FIG. 8 can extend into the page. Other trenches or cavities can be formed at a depth that extends into the page. The trenches can be created within the fluidic structure using only a portion of or the entirety of a Si wafer substrate.

Figure 14:
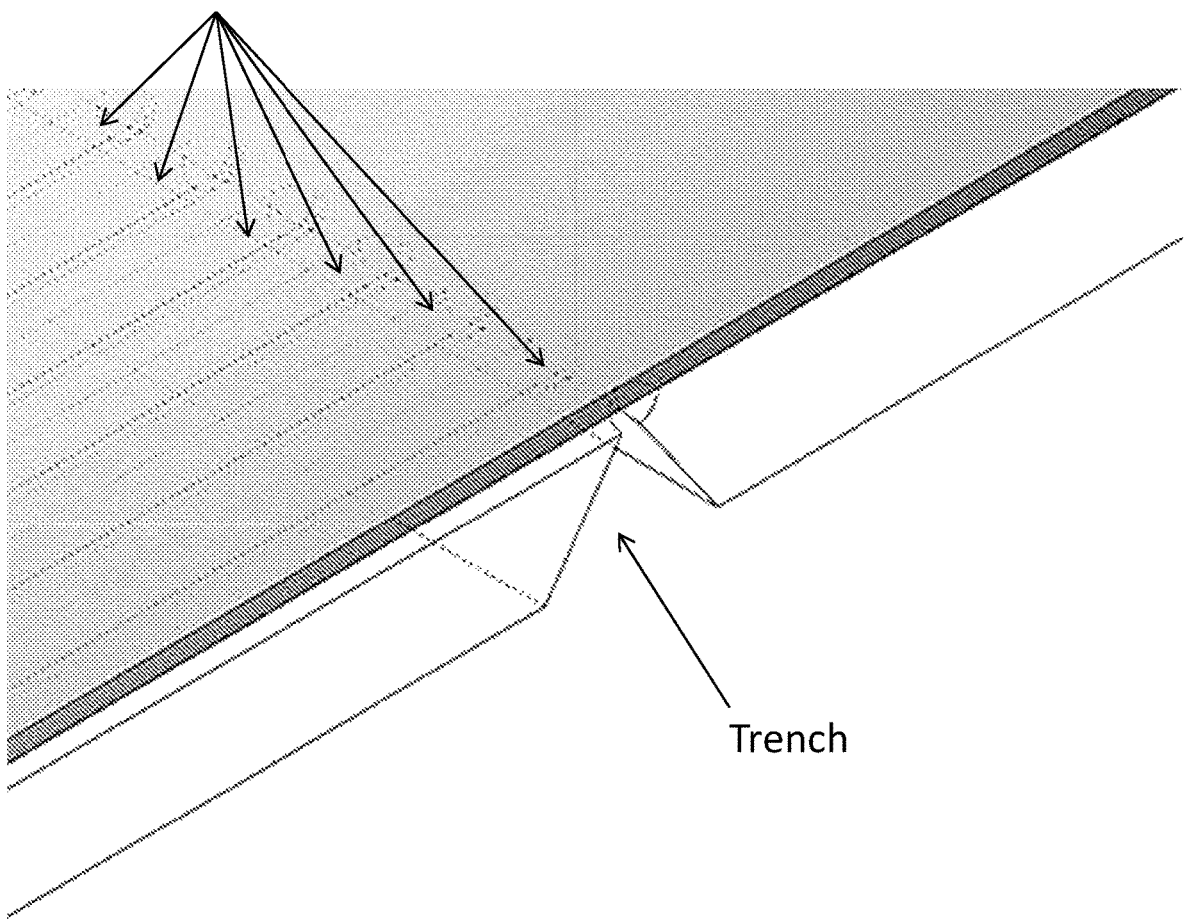
FIG. 14 is a perspective view representing the channels merging from backside to frontside (trans-membrane).

FIG. 14 is a perspective view representing the channels merging from backside to frontside (trans-membrane). FIG. 14 illustrates additional fluidic cavities in the silicon compared to, for example, FIG. 8, though both FIG. 14 and FIG. 8 illustrate a single trench. The fluidic cavities are shown in outline connected to the trench. As seen in FIG. 14, the fluidic cavity can be generally triangular in cross-section, though other shapes are possible. FIG. 14 is not drawn to scale. The fluidic cavities or other features may have other shapes or dimensions from those illustrated in FIG. 14.

In an aspect, the present disclosure provides a device comprising a monolithic structure of the present disclosure or a monolithic structure made using a method of the present disclosure. The device may have one or a plurality of such structures.

For example, the device is a filtration device. In an embodiment, the device is a filtration module for a laboratory or industrial process. In another embodiment, the device is a pre-concentration/concentration module for a laboratory or industrial process. In yet another embodiment, the device is a blood dialysis or extracorporeal membrane blood oxygenation module. Filtration and/or pre-concentration of a feed solution (e.g., blood or solutions derived from laboratory or industrial processes) can be flowed into the fluidic trenches and cavities, or above the upper most suspended membrane, and a filtrate collected on the other aspect of the suspended, porous membrane. The collected filtrate can be a portion of the feed solution that is passed through the upper most suspended membrane, as defined by its filtration properties. Alternatively, the filtrate can be collected by a dialysis process, wherein a dialysate fluid is flowed on the opposite aspect of the suspended, porous membrane to the feed solution, either in the same direction of flow or in counter-flow to the direction of flow of the feed solution. Transfer of substances between feed and filtrate solutions (i.e., dialysate solution) will occur within these devices.

In another embodiment, the devices having two suspended, porous membranes can serve as a fractionator of mixtures of differently sized solutes within a solution. For instance, one of the suspended, porous membranes could be fabricated with a filtration cut-off to retain the largest solutes within the solution, while the second suspended, porous membrane can be fabricated with a filtration cut-off to retain the middle-sized solutes within the solution. A feed solution comprised of a range of differently sized solutes can then be passed through both membranes simultaneously, permitting the fractionation of the feed solution into three size fractions. That is, the largest solutes will be retained above the first membrane, the smallest sized solutes passed by the second membrane, and the middle sized solutes retained between the two membranes.

In an embodiment, the device is a cell growth bioreactor. Cells can be disposed on the upper most suspended, porous membrane, or within the fluidic channels. Multiple cell types can be disposed on these surfaces if desired. Cell growth media can be fed into the fluidic channels or across the upper most suspended, porous membrane. The devices allow for separation of multiple cell types if co-culture is performed. As well, a biological product derived from the cells, (e.g., a secreted protein), can be collected from fluid collected from either the fluidic channels and/or above the upper most suspended, membrane, depending on device use and configuration.

In another embodiment, the device can be used as a pre-filter upstream of detector and sensor devices. For example, a detector or sensor based on the passage of an analyte of interest (e.g., one or more nucleic acids) through a single nanopore within a third distal membrane layer can be used for detection, while an upper most suspended, porous membrane can serve as a filtration membrane upstream of the single nanopore. The filtration properties of the upper most suspended, porous membrane defines the population of analyte molecules that are passed (i.e., filtered) through and presented to the single nanopore-based detector. Of course, other types of detectors and sensors that make use of membrane-based methods, such as surface-enhanced Raman spectroscopy, for example, could make use of these devices.

The steps of the methods described in the various embodiments and examples disclosed herein are sufficient to carry out the methods of the present disclosure. Thus, in an embodiment, a method consists essentially of a combination of the steps of the methods disclosed herein. In another embodiment, a method consists of such steps.

In the following Statements, various examples of the methods and structures of the present disclosure described:

Statement 1. A method for forming a monolithic structure comprising one or more suspended, nanoporous membranes comprising:
a) depositing a first membrane material layer (e.g., silicon nitride) on a first side of a substrate (e.g., a crystalline silicon wafer);
b) depositing a layer of masking material (e.g., silicon nitride) on a second side of the substrate;
c) depositing a first pre-patterning layer (amorphous silicon) on the first membrane material layer;
d) depositing a first layer of capping material (e.g., silicon oxide) on the first pre-patterning layer;
e) forming a first patterning layer (from the first pre-patterning layer) by thermal treatment of the substrate that includes the first pre-patterning layer (forming pnc-Si from the amorphous silicon layer using RTA or other thermal treatments);
f) removing the first layer of capping material;
g) patterning the first membrane material layer (to form a nanoporous membrane material) by pattern transfer from the first patterning layer by reactive ion etch;
h) optionally, removing the first patterning layer (in certain instances it is desirable to remove the first patterning layer);
i) depositing a first layer of via material (e.g., silicon oxide) on the patterned first membrane material layer;
j) patterning the first layer of via material (e.g., deposit photoresist, pattern photoresist, selectively etch silicon oxide, and remove photoresist) such that at least a portion of the patterned first membrane material layer is exposed; and
k) patterning the masking material from b), such that at least a portion of the substrate is exposed, removing at least a portion of the substrate by etching with silicon etchants (e.g., EDP, KOH, TMAH, or $XeF_2$) through the patterned first membrane material and the masking material, such that the substrate material corresponding to at least the portion of patterned first membrane material that was exposed is removed and an underlying trench and first suspended, nanoporous membrane are formed, and such that the substrate material corresponding to at least the portion of patterned masking material that was exposed is removed and a fluidic cavity is formed that is fluidically connected to the trench.

Statement 2. A method according to Statement 1, further comprising:
l) depositing a spacer layer of sacrificial (e.g., silicon, silicon oxide, or other readily removed or dissolved material) on the substrate from k) (forming a continuous layer over the first patterned via layer);
m) depositing a second membrane material layer (e.g., silicon nitride) on the layer of sacrificial material;
n) depositing a second pre-patterning layer (amorphous silicon) on the second membrane material layer;
o) depositing a second layer of capping material (e.g., silicon oxide) on the second pre-patterning layer;
p) forming a second patterning layer (from the second pre-patterning layer) by thermal treatment of substrate that includes the second pre-patterning layer (forming pnc-Si from the amorphous silicon layer using RTA or other thermal treatment);
q) removing all or substantially all of the second layer of capping material (e.g., silicon oxide);
r) patterning the second membrane material by pattern transfer from the second patterning layer by reactive ion etch;
s) optionally, removing all or substantially all of the second patterning layer;
t) depositing a second layer of via material (e.g. silicon oxide);
u) patterning the second layer of via material (e.g., deposit photoresist, pattern photoresist, selectively etch silicon oxide, and remove photoresist) such that at least a portion of the patterned second layer of membrane material is exposed;
v) removing the sacrificial material such that a second suspended, nanoporous membrane is formed (etching through the patterned second membrane layer to remove at least a portion of the sacrificial material and forming a spacer channel or a continuous fluidic cavity from the patterned area of the second via material), where the second suspended, nanoporous membrane may be in fluid contact with the first suspended, nanoporous membrane; and w) optionally, repeating steps l) to v) to form one or more additional suspended, nanoporous membranes, where one or more of the suspended, nanoporous membranes may be in fluid contact with one or more of other suspended, nanoporous membranes.

Statement 3. A monolithic structure comprising a suspended, nanoporous membrane comprising:

a substrate (e.g., a crystalline silicon wafer) having a first side and opposing second side, where the substrate has a plurality of trenches;

a patterned first membrane material layer (e.g., silicon nitride) disposed on the first side of the substrate, wherein the patterned first membrane material layer has a plurality of pores fluidically connected to the trenches in the substrate;

a first layer of via material (e.g., silicon oxide) disposed on the patterned first membrane material layer, wherein the first layer of via material is patterned to have vias fluidically connected to the pores; and a layer of masking material (e.g., silicon nitride) disposed on the second side of the substrate, wherein the layer of masking material has at least one fluidic cavity that is fluidically connected with the trenches in the substrate. In various examples, a monolithic structure is made according to any one of Statements 1 or 2.

Statement 4. A monolithic structure according to Statement 3, where the first layer of via material is absent.

Statement 5. A monolithic structure according to Statement 3, further comprising:

a first patterning layer (e.g., pnc-Si) disposed between the patterned first membrane material layer and the first layer of via material, wherein the first patterning layer is patterned to fluidically connect the vias and the pores.

Statement 6. A monolithic structure according to Statement 3, where the masking material has a plurality of the fluidic cavities, and wherein each of the trenches is fluidically connected to different fluidic cavities.

Statement 7. A monolithic structure according to Statement 3, further comprising:

a spacer layer of sacrificial material (e.g., silicon or silicon oxide) having a first side and opposing second side, wherein the spacer layer has a plurality of trenches;

a patterned second membrane material layer (e.g., silicon nitride) disposed on the first side of the spacer layer, where the patterned second membrane material layer has a plurality of pores fluidically connected to the trenches in the spacer layer; and a second layer of via material (e.g., silicon oxide) disposed on the patterned second membrane material layer, wherein the second layer of via material is patterned to have vias fluidically connected to the pores of the patterned second membrane material layer.

Statement 8. A monolithic structure according to Statement 7, where the spacer layer of sacrificial material is disposed on the patterned first membrane material layer disposed on the first side of the substrate.

Statement 9. A monolithic structure according to any one of Statements 7 or 8, wherein the spacer layer of sacrificial material is disposed on the first layer of via material disposed on the patterned first membrane material layer.

Statement 10. A monolithic structure according to any one of Statements 7 to 9, where the second layer of via material is lacking.

Statement 11. A monolithic structure according to any one of Statements 7 to 10, where the first membrane layer is a suspended, non-porous membrane.

Statement 12. A monolithic structure according to any one of Statements 7 to 11, where the first membrane layer is a suspended, porous membrane comprising a single nanopore.

Statement 13. A filtration or dialysis device comprising one or more monolithic structures of the present disclosure (e.g., one or more monolithic structures of Statements 3 or 7).

Statement 14. A method comprising performing filtration or dialysis using a filtration or dialysis device of the present disclosure (e.g., a device of Statement 13). For example, a method comprises flowing a feed solution (e.g., blood or solutions derived from laboratory or industrial processes) into the fluidic trenches and/or cavities or the upper most suspended membrane of a device such that the feed solution is filtered or pre-concentrated (e.g., by removal of one or more desirable or undesirable solutes) and, optionally, collecting the filtrate on the other aspect/side of the suspended, porous membrane (e.g., aspect/side opposite to the aspect/side contacted by the feed solution). The collected filtrate can be a portion of the feed solution that is passed through the upper most suspended membrane, as defined by its filtration properties. Alternatively, the filtrate can be collected by a dialysis process. For example, a method comprises a dialysate fluid on the opposite aspect/side of the suspended, porous membrane to that contacted by the feed solution, either in the same direction of flow or in counter-flow to the direction of flow of the feed solution, such that the feed solution is dialyzed (e.g., one or more desirable or undesirable solutes in the feed solution are removed) and, optionally, collecting the dialyzed feed solution. Transfer of substances (e.g., one or more desirable or undesirable solutes) between feed and filtrate solutions (e.g., dialysate solution) occurs within the device.

Statement 15. A cell growth bioreactor and device for recovery of derived products from grown cells comprising one or more of the monolithic structures of the present disclosure (e.g., one or more monolithic structures of Statements 3 or 7).

Statement 16. A method comprising performing cell growth and recovery of derived products from grown cells comprising use of a device of the present disclosure (e.g., a device of Statement 15). For example, a method comprises disposing cells (multiple cell types can be disposed on the surface(s)) on the upper most suspended, porous membrane and/or within the fluidic channels and feeding cell growth media into the fluidic channels or across the upper most suspended, porous membrane. The method can further comprise separation of multiple cell types, if co-culture is performed. The method can also further comprise collection of a biological product derived from the cells (e.g., a secreted protein) from fluid collected from either the fluidic channels and/or above the upper most suspended, membrane, depending on device use and configuration Statement 17. An analyte pre-filter device comprising one or more monolithic structures of the present disclosure (e.g., one or more monolithic structures of Statement 12).

Statement 18. A method comprising performing analyte pre-filtration using a device of the present disclosure (e.g., a device of Statement 17). For example, a sample (e.g., a solution) comprising an analyte of interest (e.g., one or more nucleic acids) is passed through one or more monolithic structures of the present disclosure having a single nanopore and detecting an analyte of interest (e.g., a nucleic acid) using a detector or sensor based on the passage of an analyte of interest through a single nanopore within a third distal membrane layer. In an example, the device comprises one or more suspended, porous membranes and the sample is passed through the one or more suspended, porous membranes before the single nanopore (e.g., layer comprising a single nanopore) such that solution is pre-filtered.

The invention claimed is:

1. A method for forming a monolithic structure comprising one or more suspended, nanoporous membranes comprising:
  a) depositing a first membrane material layer on a first side of a substrate;
  b) depositing a layer of masking material on a second side of the substrate;
  c) depositing a first pre-patterning layer on the first membrane material layer;
  d) depositing a first layer of capping material on the first pre-patterning layer;
  e) forming a first patterning layer by thermal treatment of the substrate that includes the first pre-patterning layer;
  f) removing the first layer of capping material;
  g) patterning the first membrane material layer by pattern transfer from the first patterning layer by reactive ion etch;
  h) depositing a first layer of via material on the patterned first membrane material layer;
  i) patterning the first layer of via material such that at least a portion of the patterned first membrane material layer is exposed; and
  j) patterning the masking material from b), such that at least a portion of the substrate is exposed, removing at least a portion of the substrate by etching with silicon etchants through the patterned first membrane material and the masking material, such that the substrate material corresponding to at least the portion of patterned first membrane material that was exposed is removed and an underlying trench and first suspended, nanoporous membrane are formed, and such that the substrate material corresponding to at least the portion of patterned masking material that was exposed is removed and a fluidic cavity is formed that is fluidically connected to the trench.

2. The method of claim 1, further comprising:
  k) depositing a spacer layer of sacrificial material on the substrate from j);
  l) depositing a second membrane material layer on the layer of sacrificial material;
  m) depositing a second pre-patterning layer on the second membrane material layer;
  n) depositing a second layer of capping material on the second pre-patterning layer;
  o) forming a second patterning layer by thermal treatment of substrate that includes the second pre-patterning layer;
  p) removing all or substantially all of the second layer of capping material;
  q) patterning the second membrane material by pattern transfer from the second patterning layer by reactive ion etch;
  r) depositing a second layer of via material;
  s) patterning the second layer of via material such that at least a portion of the patterned second layer of membrane material is exposed; and
  t) removing the sacrificial material such that a second suspended, nanoporous membrane is formed, wherein the second suspended, nanoporous membrane may be in fluid contact with the first suspended, nanoporous membrane.

3. The method of claim 2, further comprising, after step q):
  removing all or substantially all of the second patterning layer.

4. The method of claim 2, further comprising, after step t):
  repeating steps k) to t) to form one or more additional suspended, nanoporous membranes, wherein one or more of the suspended, nanoporous membranes may be in fluid contact with one or more of other suspended, nanoporous membranes.

5. The method of claim 1, further comprising, after step g):
  removing the first patterning layer.

* * * * *